(12) United States Patent
Acevedo et al.

(10) Patent No.: US 10,882,930 B2
(45) Date of Patent: Jan. 5, 2021

(54) BIOMOLECULE-FUNCTIONALISED PVC AND PRODUCTION METHOD THEREOF

(71) Applicant: Universidad De Chile, Santiago (CL)

(72) Inventors: Marcela Urzúa Acevedo, Santiago (CL); Carolina Sandoval Rocuant, Santiago (CL); Mehrdad Yazdani-Pedram Zobeiri, Santiago (CL); Rafael Martinez Figueroa, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 64 days.

(21) Appl. No.: 16/346,830

(22) PCT Filed: Nov. 2, 2017

(86) PCT No.: PCT/IB2017/056823
§ 371 (c)(1),
(2) Date: May 1, 2019

(87) PCT Pub. No.: WO2018/083623
PCT Pub. Date: May 11, 2018

(65) Prior Publication Data
US 2020/0062872 A1 Feb. 27, 2020

(30) Foreign Application Priority Data
Nov. 2, 2016 (CL) .................. 201602771

(51) Int. Cl.
*C08F 14/06* (2006.01)
*A61L 29/08* (2006.01)

(52) U.S. Cl.
CPC ............ *C08F 14/06* (2013.01); *A61L 29/085* (2013.01)

(58) Field of Classification Search
None
See application file for complete search history.

(56) References Cited

U.S. PATENT DOCUMENTS 5,053,453 A * 10/1991 Ku .................. A61K 35/62
523/112
2020/0062872 A1 * 2/2020 Acevedo .................. C08F 8/32

OTHER PUBLICATIONS

Covalent Immobilization of b-Galactosidase onto amino-functional PVC microspheres, Eldin et al. (Year: 2010).*
Bolduc, et al., "Monolayers of 3-Mercaptopropyl-amino Acid to Reduce the Nonspecific Adsorption of Serum Proteins on the Surface of Biosensors," *Langmuir*, vol. 24, No. 20, pp. 12085-12091 (2008). [Abstract].
Statz, et al., "Protein, cell and bacterial fouling resistance of polypeptoid-modified surfaces: effect of side-chain chemistry," vol. 4, No. 1, pp. 131-139 (2008). [Abstract].

(Continued)

*Primary Examiner* — Peter A Salamon
(74) *Attorney, Agent, or Firm* — Foley & Lardner LLP

(57) ABSTRACT

The present invention relates to the medical industry. In particular, it is related to a polyvinyl chloride polymer (PVC) functionalized for medical use, which is flexible and compatible with blood. Specifically, this invention is related to a biomolecule-functionalized PVC and its production method, in order to produce a flexible and blood-compatible polymer for medical use.

8 Claims, 8 Drawing Sheets

(56) References Cited

OTHER PUBLICATIONS

Asadinezhad, et al., "Recent Progress in Surface Modification of Polyvinyl Chloride," *Materials*, vol. 5, No. 12, pp. 2937-2959 (2012).
Damodaran, et al., "Bio-inspired Strategies for Designing Antifouling Biomaterials," *Biomaterials Research*, vol. 20, No. 1, p. 18 (Jun. 2016).
International Preliminary Report on Patentability issued in International Patent Application No. PCT/IB2017/056823, dated May 7, 2019.
International Search Report issued in International Patent Application No. PCT/IB2017/056823, dated Feb. 27, 2018.

\* cited by examiner

BIOMOLECULE-FUNCTIONALISED PVC AND PRODUCTION METHOD THEREOF

CROSS-REFERENCE TO RELATED APPLICATIONS

This application is a U.S. National Stage of International Patent Application No. PCT/IB2017/056823, filed Nov. 2, 2017, which claims priority from Chile Patent Application No. 201602771, filed Nov. 2, 2016. The contents of these applications are incorporated herein by reference in their entirety.

FIELD OF THE INVENTION

The present invention relates to the medical industry. In particular, it is related to a functionalized polyvinyl chloride (PVC) polymer for medical use, which is flexible and compatible with blood.

Specifically, this invention is related to a biomolecule-functionalized PVC and method of production thereof, for the purpose of producing a flexible and blood-compatible polymer for medical use. Biomolecules used to functionalize this PVC correspond to amino acids having a hydropathic index between −3.5 and 1.8.

STATE OF THE ART

Poly(vinyl chloride) (PVC) is one of the most used polymers in the world, since its properties such as high resistance to chemical agents, low solubility and low cost, enable them to be applied in various fields such as construction, packaging, electricity and medicine.

For a polymer to be used in medicine, specifically, in blood storage devices, catheters, tubes, etc. in contact with blood, the polymer must comply with certain mechanical properties. In the specific case of PVC, PVC should have the required flexibility which is achieved through the use of plasticizers. Currently, di-(2-ethylhexyl)phthalate (DEHP) is the most used plasticizer in medical devices, such as blood storage bags, hoses, tubes, intravenous catheters, since it provides the necessary flexibility to PVC. However, DEHP has disadvantages such as acute toxicity for animals and humans, wherein blood DEHP tolerable daily concentration is 48 µg/L per day. The main problem is that DEHP releases from blood storage bags and enters the body because is not covalently bound to PVC, thus generating adverse health effects. In medical devices, such as blood storage bags, additive DEHP concentration during dialysis and blood transfusion processes exceeds 2,200 µg/L per day. That is, it exceeds 40 times the tolerable daily dose. The present invention allows to reduce or avoid the use of DEHP in PVC, while maintaining or increasing flexibility of said PVC.

Blood compatibility is other property that polymers used in medical devices should have. Blood compatibility is related to the resistance to generating clots on the surface of a material. Coagulation is a process that begins with the adhesion and activation of blood platelets. Therefore, a polymer that resists platelet adhesion on its surface will prevent clot formation and will be more blood-compatible. It has been proven that platelet adhesion on a surface is directly related to surface wettability. Thus, a hydrophobic surface in contact with blood will have greater platelet adhesion, and a less hydrophobic surface will be more resistant to platelet adhesion. PVC is not compatible with blood; therefore, additives again play an important role in improving a property and allowing the use of PVC in medicine.

The present invention uses chemical modification as an alternative to improve blood compatibility of PVC by chemically modifying PVC by functionalization with hydrophilic molecules, this will increase wettability of PVC film surface and improve its blood compatibility. In this way, the solution provided by the present invention consists of avoiding or diminishing the use of flexibility additives, of which DEHP is the main one.

PVC is white and has a density between 1.38 and 1.40 g/cc. Its melting temperature depends on polymerization degree and varies from 80 to 85° C. PVC in the polymerization process can reach molecular weights of about 200,000 g/mol.

PVC solubility depends on molecular weight. Thus, PVC having molecular weights above 180,000 g/mol is only soluble in organic solvents such as cyclohexanone, methylcyclohexanone, tetrahydrofuran (THF) and chlorobenzene. PVC is resistant to water and chemical agents (cold alkaline bases, concentrated acids and ozone). However, it has low heat and light resistance, gradually decomposing with loss of hydrochloric acid and subsequent double bond oxygenation. PVC low thermal stability is mainly due to the structural defects contain therein. These defects are the main points where the dehydrochlorination reaction occurs generating conjugated polyenes and causing eventual loss of PVC properties.

To avoid dehydrochlorination and improving PVC properties, which allow its processing and application, it is necessary to use certain additives:

a) Stabilizers for preventing its degradation during processing, which correspond to antioxidants, and hydrochloric acid "trapping" compounds: alkaline or alkaline earth metal carbonates, phosphates, stearates, sodium lactate, calcium silicate, etc.

b) Lubricants for preventing PVC adhesion to processing machinery surface. Stearic acid, metal stearates, fatty acid esters and low molecular weight polyethylenes are used.

c) Plasticizers for increasing its flexibility. Phthalates such as di-(2-ethylhexyl)phthalate (DEHP), Diisodecyl-phthalate (DIDP) and Diisononyl-phthalate (DINP) are used, among others.

PVC application will be determined by the amount and type of additives used.

PVC has currently a wide range of applications in various fields. In the medicine field, PVC is used in blood storage bags, catheters, tubes, etc.

Materials used in medical devices, such as blood storage devices, catheters, tubes, etc., in addition to having some flexibility should be blood-compatible. Blood compatibility is related to the ability of the material to prevent blood clots upon contact with blood. Typically, when vascular damage occurs, surrounding platelets bind to collagen fibers at the damaged sites and clots are formed. Then, platelets are activated losing their shape and surface roughness. These events are balanced by inherent anticoagulant processes. However, clot formation on a synthetic surface reflects the poor compatibility between said material and blood. Fibrinogen is the central protein in the coagulation process induced by a material. Platelets adhere on this protein and are then activated forming thrombi.

Material surface properties affect adsorption, structure and function of proteins involved in coagulation process. Decisive surface properties are: surface free energy and wettability, surface chemical nature, and topography (see FIG. 1). Wettability generally includes all phenomena involved in the contact between three phases, of which at least two are fluid (liquid or gas). A typical case is a liquid wetting a solid surface in a gaseous environment. Wettability is directly related to surface energy. Wettability of a solid surface is greater the smaller the contact angle and, therefore, surface energy will be lower. That is, a hydrophilic surface will have a lower surface energy than a hydrophobic surface.

Hydrophobic surfaces generally tend to absorb more protein than hydrophilic surfaces (see FIG. 2). That is, surfaces with a low surface energy are more resistant to platelet adhesion and more compatible with blood.

The present invention relates to PVC functionalization to improve the properties of said polymer such as flexibility and blood compatibility, because it helps to avoid or reduce the use of plasticizers harmful to human health.

U.S. Pat. No. 5,053,453 A, dated Oct. 1, 1991, discloses thromboresistant materials comprising hirudin or hirudin derivatives covalently linked to support materials such that the resulting composition has substantially the same biological activity as hirudin. Methods for making such compositions are also described. The thromboresistant material comprises a protein having an amino acid sequence sufficiently complementary to the hirudin binding sites to thrombin such as those having thrombotic activity, covalently linked to a support material through a binding group, wherein the support material is a polymer. Used polymers including PVC mixed with 30-40% w/w of plasticizers such as di-(2-ethylhexyl)phthalate (DEHP).

SUMMARY OF THE INVENTION

The present invention relates to the functionalization of PVC of different molecular weight (less than 200,000 g/mol), with amino acids having hydropathic index between −3.5 and 1.8, in order to increase PVC hydrophilic nature and thus increase its blood compatibility. In addition, these functionalizations make possible to incorporate side chains to PVC increasing its flexibility, which allows reducing or avoiding the use of plasticizers in blood storage bags.

Polymeric films using PVC functionalized with Gly or β-Ala are less hydrophobic than non-functionalized PVC films.

Similarly, polar part contribution is greater in PVC films functionalized with amino acids having hydropathic index between −3.5 and 1.81, especially with amino acids Gly or β-Ala, relative to non-functionalized PVC.

Platelet adhesion assays of PVC films functionalized with amino acids having hydropathic index between −3.5 and 1.81, especially with amino acids Gly or β-Ala, found these to be blood-compatible.

According to the tensile tests carried out, flexibility of functionalized PVC result to be greater than non-functionalized PVC In summary, it can be concluded that from a PVC functionalized with the amino acids of hydropathic index between −3.5 and 1.81, specifically with amino acids Gly or β-Ala, could be obtain more flexible and blood-compatible polymer films relative to non-functionalized PVC. This allows producing a material for medical use, such as blood storage bags, catheters, tubes, etc., having less or no percentage of plasticizers.

DETAILED DESCRIPTION OF THE INVENTION

The present invention discloses polymer films for medical use, which are composed of PVC functionalized with an amino acid (Aa) for producing blood-compatible, higher flexibility polymer films.

The method for producing this functionalized PVC comprises the following steps:
i. mixing a PVC having molecular weight less than 200,000 g/mol with an amino acid selected from the group of amino acids having hydropathic index between −3.5 and 1.8 and with a catalyst selected from the group of carbonates of alkali salts at 1:1:1 to 2:2:1, preferably 3:3:2 molar ratio, in a dissolution solvent and under an inert atmosphere;
ii. stirring the mixture at 1,000 rpm under a constant temperature between 50° C. and 120° C. for a time between 20 and 120 minutes;
iii. adding a polymer in a precipitation solvent.
iv. centrifuging between 5,000 and 12,000 rpm for 10 to 60 minutes at 25° C. temperature;
v. purifying functionalized polymer by dissolving in a dissolution solvent and precipitation in a precipitation solvent and drying to constant mass.

The molecular weight of the PVC used in step i) is selected from 43,000, 80,000 and 161,000 g/mol.

From the group of amino acids having hydropathic index between −3.5 and 1.8, the amino acids used in step i) are selected from Gly or β-Ala.

Lithium carbonate (Li$_2$CO$_3$), sodium carbonate (Na$_2$CO$_3$), potassium carbonate (K$_2$CO$_3$) are within the group of alkaline carbonates.

The dissolution solvent used in steps i) and v) is selected from dimethyl sulfoxide (DMSO) anhydrous, cyclohexanone, dichlorobenzene, dimethylformamide.

The precipitation solvent used in steps iii) and v) comprises Methanol/Water (MeOH/H$_2$O) or Ethanol/Water (EtOH/H$_2$O) at 2:1 v/v ratio.

A gas selected from nitrogen, argon, etc. is used to achieve an inert atmosphere in step (i).

In addition, optionally adding a plasticizer to the mixture of step i), such as di-(2-ethylhexyl)phthalate (DEHP) in an amount of less than 10% w/v, specifically 10% w/w.

Molecular identification of the PVC functionalized with an amino acid selected from the group of amino acids having hydropathic index between −3.5 and 1.8, was made by Fourier Transform Infrared Spectroscopy (FT-IR), proton nuclear magnetic resonance ($^1$HNMR) and solid state carbon-13 ($^{13}$C NMR), elemental analysis, thermogravimetric analysis (TGA) and differential scanning calorimetry (DSC).

tion band corresponding to the N—H stretch should appear around at 3,300 cm$^{-1}$, which is probably coupled with the band associated with the hydroxyl group. It is observed that the absorption band intensity associated with the C═C bond is greater than those related to the amino acid residues bound to the polymer backbone. The absorption band corresponding to the C—Cl stretch is observed around at 685 cm$^{-1}$, the intensity of which decreases in the functionalized PVCs.

Figure 4:
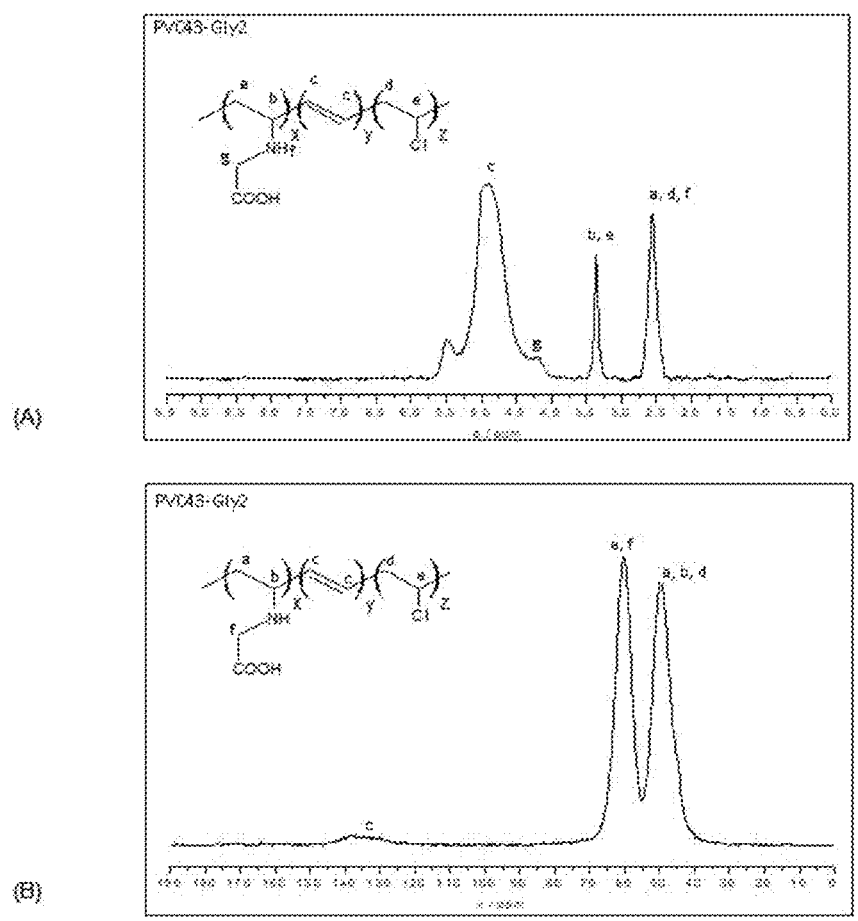
FIG. 4 shows spectra (A) $^1$H NMR and (B) $^{13}$C NMR for PVC43-Gly2 (time 2 of 120 min).

FIG. 4 shows an intense signal at 5 ppm, which corresponds to olefin protons (—CH═CH—) present in a large part of the polymer chain. A signal at 2.5 ppm corresponding to the proton of the amino group (—NH) is also seen, which indicates amino acid incorporation into PVC chain. This signal is coupled with the signal associated with methylene protons (—CH$_2$—) of the polymer backbone. Signal at 3.3 ppm corresponds to a coupling of the signals associated with the methine proton linked to the amino acid residue (CH—N) and the methine proton linked to the chlorine atom (CH—Cl). Signal at 4.2 ppm is associated with the methylene proton of the amino acid residue.

Figure 5:
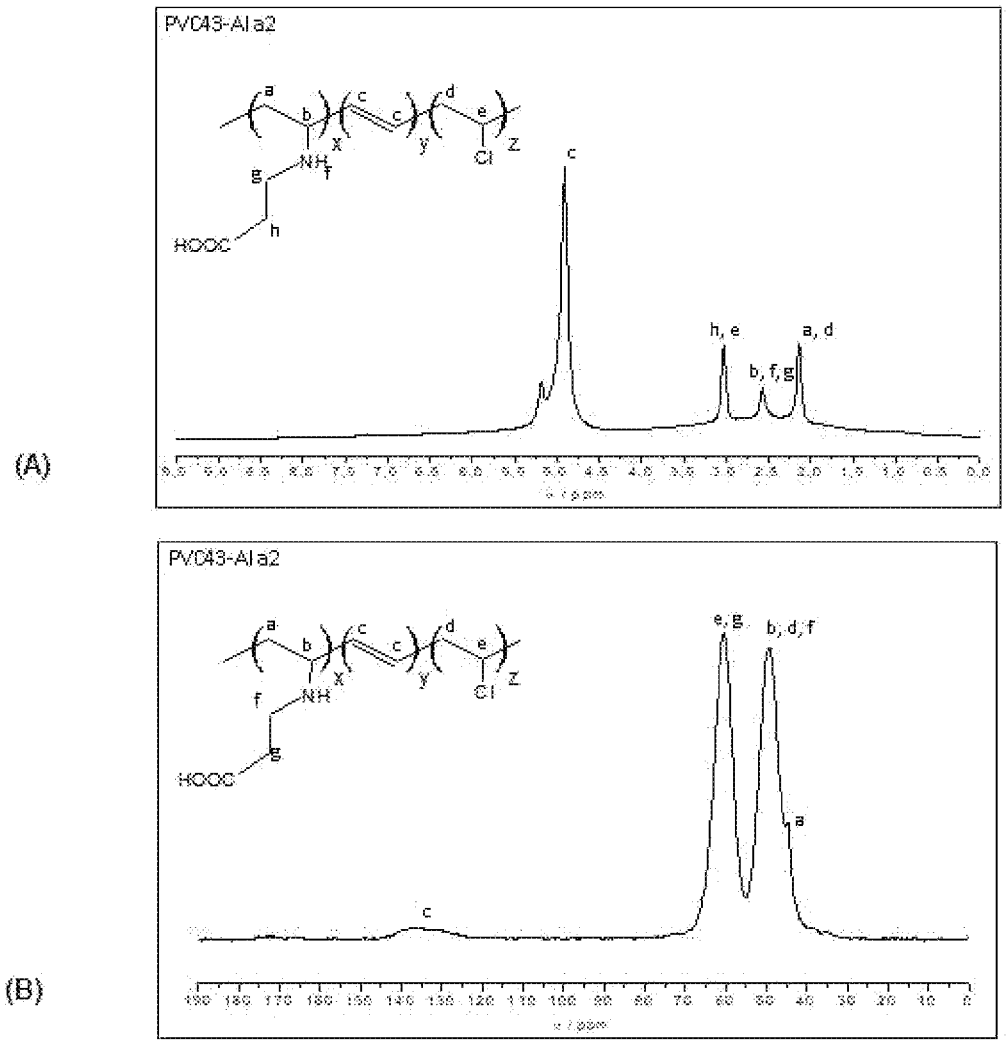
FIG. 5 shows spectra (A) $^1$H NMR and (B) $^{13}$C NMR for PVC43-Ala2 (time 2 of 40 min).

FIG. 5 shows the presence of methine and methylene carbons, the signals of which are between 40 and 70 ppm. In addition, a signal at 135 ppm is seen which corresponds to

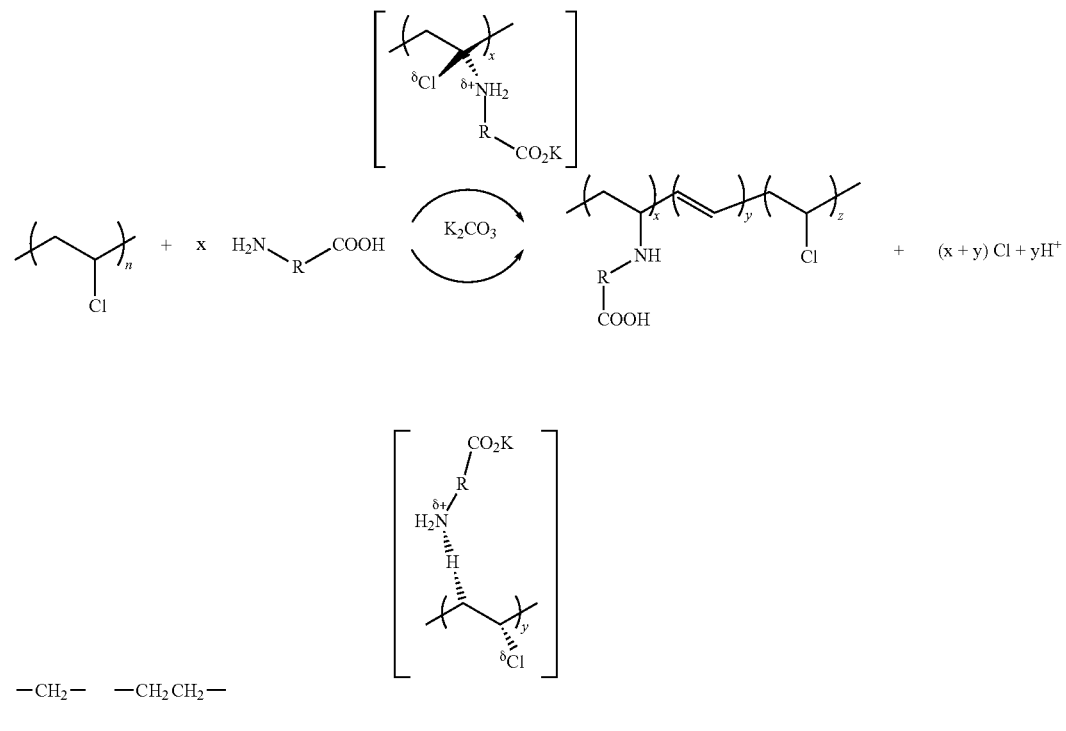

R:  —CH$_2$—   —CH$_2$CH$_2$—

Glycine    β-Alanine

* x = 0.10
** y = 0.85
*** z = 0.05

Figure 1:
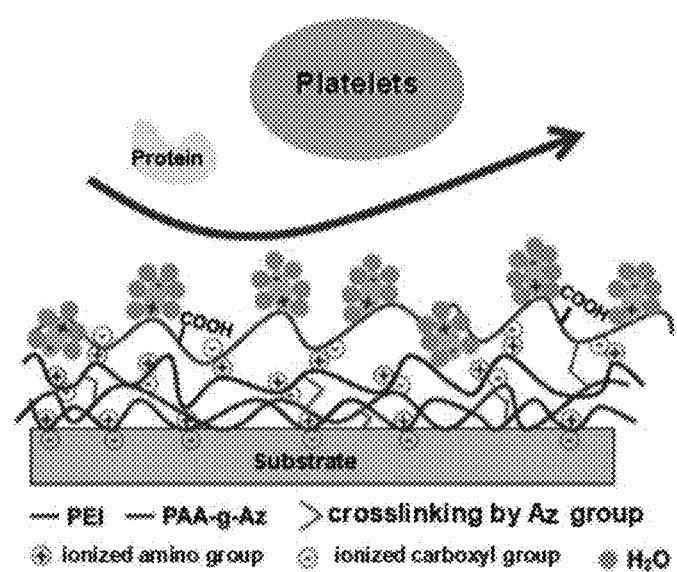
FIG. 1 is drawing showing observed decrease in fibrinogen adsorption and platelet adhesion on a modified surface.
Figure 2:
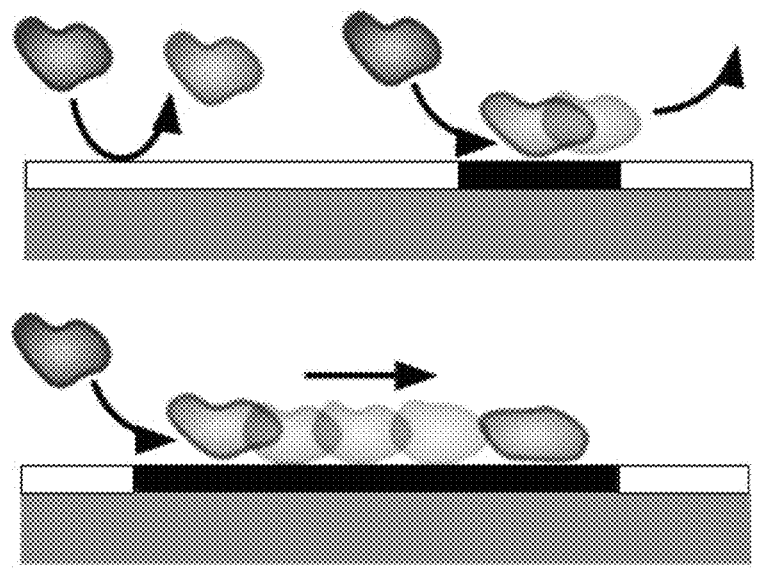
FIG. 2 shows a schematic drawing of protein adsorption in hydrophobic domains (black) in a hydrophilic matrix (white).
Figure 3:
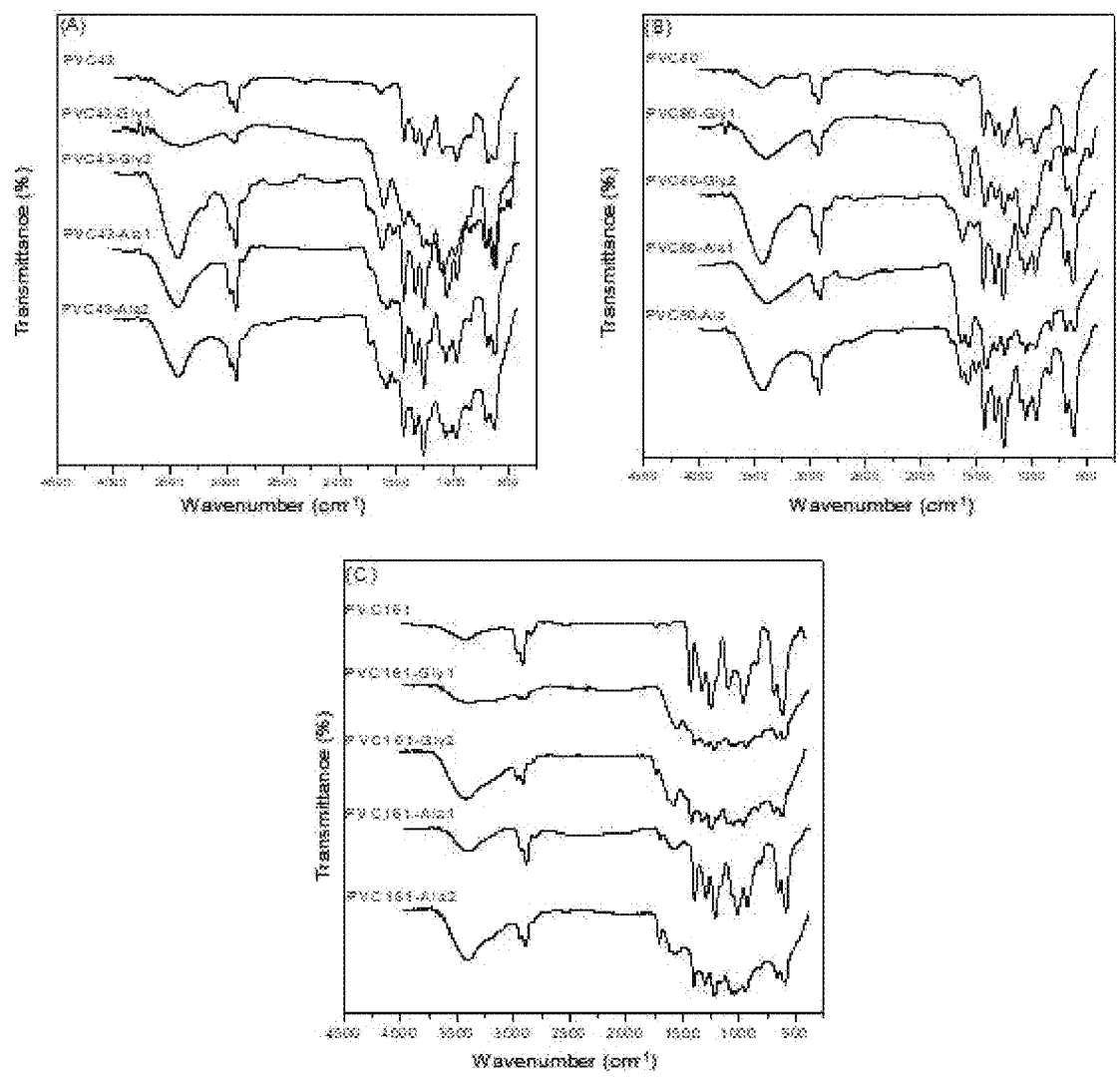
FIG. 3 shows FT-IR spectra of (A) PVC of 43,000 g/mol (PVC43), (B) PVC of 80,000 g/mol (PVC80) and (C) PVC of 161,000 g/mol (PVC161) non-functionalized and functionalized with amino acids Gly and β-Ala. Two reaction times of product preparation are shown for each functionalization, i.e., when using Gly at reaction times of 60 and 120 min (time 1 and 2 respectively, assigned as PVC43-Gly1, PVC80-Gly1 and PVC161-Gly1, for time 1, and PVC43-Gly2, PVC80-Gly2 and PVC161-Gly2 for time 2) and when using β-Ala at reaction times of 20 and 40 min (time 1 and 2, respectively).

FT-IR spectra of FIG. 3 shows that in the functionalized PVC samples, the absorption band corresponding to the C═C stretch appears around at 1,630 cm$^{-1}$. On the other hand, in each functionalized PVC, the absorption band corresponding to the C═O stretch is around 1,734 cm$^{-1}$ and a wide absorption band at around 3,340 cm$^{-1}$ corresponding to the O—H stretch vibration is also observed. The absorpthe olefin carbons (CH═CH) in the polymer chain. This again demonstrates the amino acid functionalization of PVC and the presence of unsaturations in the polymer backbone.

Elemental Analysis

An elemental analysis was carried out to assess the functionalization degree (FD) of some functionalized polymers

TABLE 1

Percentages of nitrogen, carbon and hydrogen obtained by elemental analysis of PVC43, PVC80 and PVC161 functionalized with Gly and β-Ala.

| Polymer | N (%) | C (%) | H (%) |
|---|---|---|---|
| PVC43-Gly1 | 1.08 | 35.94 | 4.33 |
| PVC43-Gly2 | 1.46 | 34.02 | 4.70 |
| PVC43-Ala1 | 0.26 | 36.73 | 4.56 |
| PVC43-Ala2 | 3.93 | 39.27 | 5.66 |
| PVC80-Gly1 | 1.32 | 36.03 | 4.53 |
| PVC80-Gly2 | 2.57 | 35.09 | 4.66 |
| PVC80-Ala1 | 0.57 | 40.82 | 5.22 |
| PVC80-Ala2 | 1.18 | 34.22 | 4.35 |
| PVC161-Gly1 | 0.42 | 37.01 | 4.76 |
| PVC161-Gly2 | 0.54 | 37.17 | 4.81 |
| PVC161-Ala1 | 0.55 | 39.83 | 5.14 |
| PVC161-Ala2 | 0.75 | 37.50 | 4.98 |

Functionalization degrees listed on Table 2 are obtained through the following mathematical calculations.

Calculation of Functionalization Degree (FD)

To calculate FD, we must consider the hypothetical case in which PVC is 100% functionalized with the used amino acid.

For example, when using β-Ala, the 100% functionalized polymer would be the following:

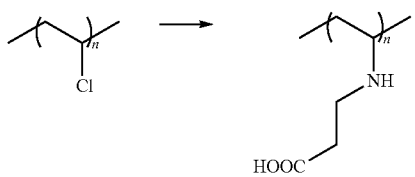

First, molecular weight of the PVC monomer unit ($Ur_0$=62.5 g/mol) and the functionalized polymer ($Ur_{100}$=115 g/mol) should be considered.

Then, mass percentage of nitrogen present in each monomeric unit should be calculated. For PVC, % N=0 and for the functionalized polymer, % N=12.2.

Subsequently, we use the straight line equation % N=m·Ur+b, where m is the slope and b the intercept (both constants) and Ur is the molecular weight of the monomeric unit of the polymer of unknown FD, for constructing an equation system, as follows:

0=m·62.5+b applies when there is no functionalization
12.2=m·115+b applies when there is 100% functionalization m and b values are then obtained as m=0.232, b=−14.5

Then, for the β-Ala-functionalized PVC, we have the following relationship:

$$\%N = 0.232 \cdot Ur - 14.5 \quad (A1)$$

Wherein Ur is the molecular weight of the monomeric unit of the polymer having unknown functionalization degree and % N is the polymer nitrogen mass percentage, this values is obtained by elemental analysis.

For PVC80-Ala1, elemental analysis shows that % N=0.592. This value is replaced in the equation A1 to obtain Ur=65.0 g/mol.

Subsequently, we use the relationship $Ur = Ur_0 \cdot x + Ur_{100} \cdot y$, wherein x is the non-functionalized polymer fraction and y is the functionalized polymer fraction.

From the above, a second equation system is constructed as follows:

$$65.0 = 62.5 \cdot x + 115 \cdot y$$

$$x+y=1$$

x and y values are then obtained as x=0.951, y=0.0486

Finally, when expressing the y value in percentage, we have FD=4.9%.

TABLE 2

Functionalization degrees of PVC functionalized with Gly and β-Ala.

| Polymer | FD (%) | Polymer | FD (%) | Polymer | FD (%) |
|---|---|---|---|---|---|
| PVC43-Gly1 | 7.8 | PVC80-Gly1 | 9.5 | PVC161-Gly1 | 3.0 |
| PVC43-Gly2 | 10.5 | PVC80-Gly2 | 18.5 | PVC161-Gly2 | 3.9 |
| PVC43-Ala1 | 2.3 | PVC80-Ala1 | 4.9 | PVC161-Ala1 | 4.7 |
| PVC43-Ala2 | 32.5 | PVC80-Ala2 | 9.9 | PVC161-Ala2 | 6.3 |

Table 2 shows PVC amino acid functionalization degrees obtained. Low FD is attributed to low nucleophilicity of the amino group in each amino acid.

Furthermore, from Table 2 can be seen that when functionalizing PVC43, PVC80 and PVC161 with amino acids Gly, β-Ala there is a relationship between FD and reaction time. In general, FD is higher the longer the time of reaction. That is to say, when the reaction time is longer there is a greater incorporation of amino acid molecules in the PVC chain and, therefore, FD is higher.

A relationship between functionalization degree and PVC molecular weight is also seen. Generally, higher FDs are obtained when using PVC80, and lower FDs are obtained when using PVC161. This is due to the curled shape adopted by polymers in solution. Higher molecular weight curled PVC will have less available active sites where the substitution reaction could occur, therefore, will result in less functionalized polymers.

Thermogravimetric Analysis

Figure 6:
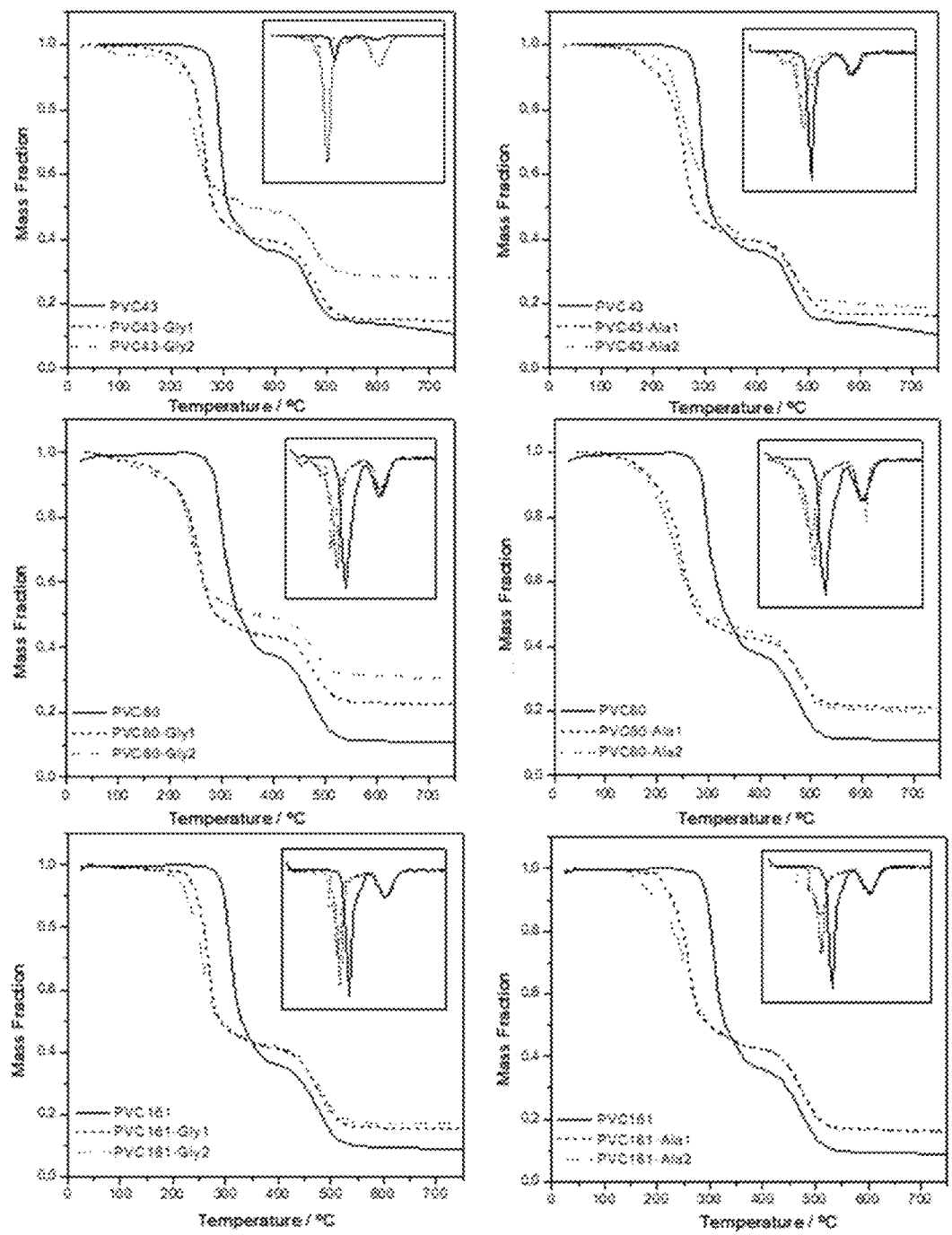
FIG. 6 shows thermal degradation profiles for PVC43, PVC80 and PVC161 functionalized with Gly and β-Ala.

Thermogravimetric analyzes were carried out to study the effect of PVC functionalization on polymer thermal stability and to corroborate the presence of amino acid residues in the backbone. FIG. 6 shows PVC thermal degradation profiles, PVC functionalized with Gly and β-Ala.

FIG. 6 shows that thermal degradation profiles of PVC43, PVC80 and PVC161 are similar to functionalized PVC. First PVC thermal decomposition temperature ($TDT_1$) corresponds to the loss of chlorine atoms. The second one ($TDT_2$) is associated with the break of the polymer backbone, causing the loss of up to 90% of the initial mass. In the case of functionalized PVC, $TDT_1$ can be attributed to the break of amino acid residues bound to the PVC backbone, which can occur in conjunction with the loss of chlorine atoms. In these cases, $TDT_2$ is also attributed to the break of the backbone.

Table 3 shows the thermal decomposition temperature of polymer systems.

TABLE 3

Thermal decomposition temperatures ($TDT_1$ and $TDT_2$) for PVC43, PVC80 and PVC161 non-functionalized and functionalized with amino acids Gly and β-Ala.

| Polymer | $TDT_1$ (° C.) | $TDT_2$ (° C.) |
|---|---|---|
| PVC43 | 297 | 467 |
| PVC43-Gly1 | 264 | 476 |
| PVC43-Gly2 | 248 | 470 |
| PVC43-Ala1 | 261 | 477 |

TABLE 3-continued

Thermal decomposition temperatures ($TDT_1$ and $TDT_2$) for PVC43, PVC80 and PVC161 non-functionalized and functionalized with amino acids Gly and β-Ala.

| Polymer | $TDT_1$ (° C.) | $TDT_2$ (° C.) |
| --- | --- | --- |
| PVC43-Ala2 | 244 | 474 |
| PVC80 | 306 | 467 |
| PVC80-Gly1 | 258 | 480 |
| PVC80-Gly2 | 245 | 472 |
| PVC80-Ala1 | 253 | 478 |
| PVC80-Ala2 | 241 | 478 |
| PVC161 | 308 | 475 |
| PVC161-Gly1 | 268 | 472 |
| PVC161-Gly2 | 258 | 474 |
| PVC161-Ala1 | 261 | 474 |
| PVC161-Ala2 | 259 | 475 |

Table 3 shows that $TDT_1$ of functionalized PVC is lower than $TDT_1$ of the corresponding PVC. This confirms that there is an alteration in polymer stability due to incorporation of amino acids into the PVC backbone. This effect is due to the fact that the C—Cl bond energy (339 kJ/mol) in PVC is higher than C—N bond energy (305 kJ/mol) of the functionalized PVC.

In addition, it can be seen, in general, that there is no significant variation in the $TDT_2$ of functionalized polymers, compared with that of non-functionalized PVC. This could be indicative that there are no significant structural changes in the polymer backbone.

Table 3 further shows that there is a relationship between $TDT_1$ of functionalized polymers and reaction time. In all cases, $TDT_1$ is lower when the reaction time is longer. This behavior indicates that when the reaction time increases, there is a greater incorporation of amino acids in the PVC backbone and, as a consequence, a slight decrease in thermal stability. These results agree with the functionalization degree obtained by elemental analysis.

Furthermore, it can be seen, in general, that $TDT_2$ of functionalized PVC43 and PVC80 polymers is slightly higher compared to PVC43 and PVC80. This result again evidences the presence of double bonds in the backbone of the functionalized polymers. This effect is due to the fact that C═C bond energy (614 kJ/mol) is higher than the C—C bond energy (347 kJ/mol). $TDT_2$ of functionalized PVC161 polymers does not have a significant difference relative to PVC161. This indicates that functionalized PVC161 polymers have a lower number of double bonds in their backbone, compared to functionalized PVC43 and PVC80.

Differential Scanning Calorimetry

Figure 7:
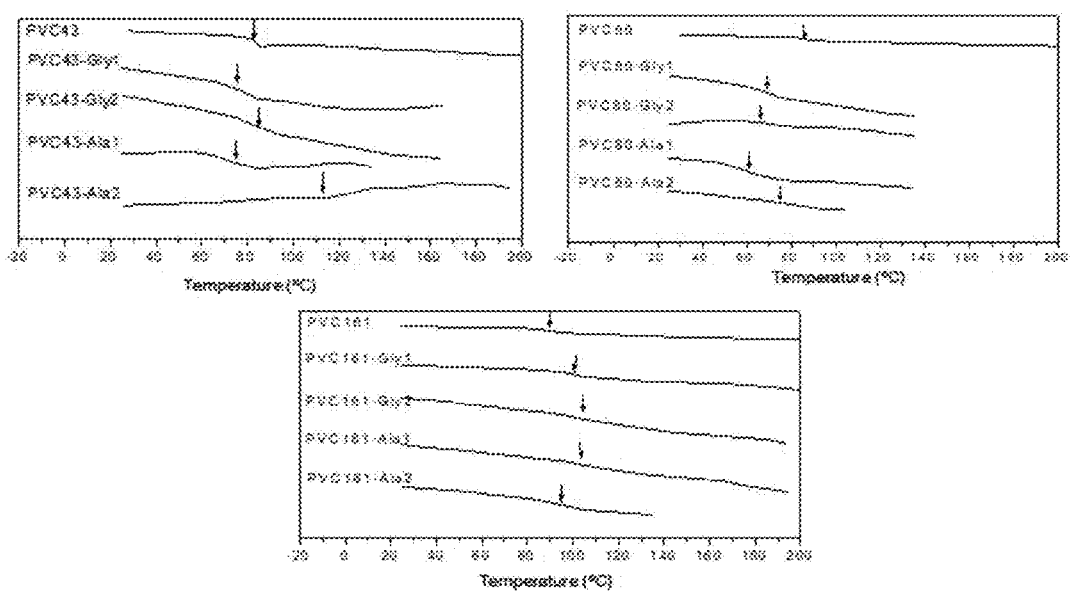
FIG. 7 shows differential scanning calorimetry (DSC) thermograms for PVC43, PVC80 and PVC161 non-functionalized and functionalized with amino acids Gly and β-Ala at two reaction times each, i.e., Gly is used at reaction times of 60 and 120 min (time 1 and 2, respectively) and β-Ala is used at reaction times 20 and 40 min (time 1 and 2, respectively).

FIG. 7 shows that when PVC80 is functionalized with Gly or β-Ala, Tg value decreases, but when PVC161 is similarly functionalized, Tg value increases. These results are related to FD values shown in Table 2. For example, FD for PVC80-Gly1 and PVC80-Gly2 is 6.7 and 15.6%, respectively, while for PVC161-Gly1 and PVC161-Gly2 is 2.1 and 2.7%, respectively. This indicates functionalized PVC80 has a greater amount of amino acid residues in the backbone, which generates an increase in the polymer free volume, a greater freedom of movement between molecules and therefore, a lower Tg. On the other hand, those functionalized PVC161 having very low functionalization and probably a large number of double bonds in the backbone, have an increased packaging relative to the non-functionalized polymer, Tg then increases.

Table 4 shows Tg values for each polymer. A relationship between molecular weight and Tg is seen for non-functionalized polymers. Lower molecular weight polymers have lower Tg values. This is because a lower molecular weight polymer has a greater number of chain ends, which have greater mobility than intermediate segments. This results in shorter polymer chains needing less energy to move over each other, reflected in lower values of Tg.

TABLE 4

Glass transition temperatures (Tg) for PVC43, PVC80 and PVC161 non-functionalized and functionalized with amino acids Gly and β-Ala at reaction times 1 and 2. Each functionalization was carried out at two reaction times, i.e., reaction times were 60 and 120 min (time 1 and 2, respectively) when using Gly and reaction times were 20 and 40 min (time 1 and 2, respectively) when using β-Ala.

| Polymer | Tg (° C.) | Polymer | Tg (° C.) | Polymer | Tg (° C.) |
| --- | --- | --- | --- | --- | --- |
| PVC43 | 83 | PVC80 | 87 | PVC161 | 92 |
| PVC43-Gly1 | 76 | PVC80-Gly1 | 69 | PVC161-Gly1 | 101 |
| PVC43-Gly2 | 84 | PVC80-Gly2 | 68 | PVC161-Gly2 | 104 |
| PVC43-Ala1 | 75 | PVC80-Ala1 | 61 | PVC161-Ala1 | 103 |
| PVC43-Ala2 | 116 | PVC80-Ala2 | 75 | PVC161-Ala2 | 96 |

Table 4 shows that functionalized PVC43 and PVC80 have lower Tg values relative to the corresponding non-functionalized PVCs. This is due to the insertion of molecules of greater volume than the Cl atom in the PVC backbone, which generate an increase in polymer free volume, produce less packing and lower Tg.

Tg may indicate relative flexibility of polymers. Thus, a polymer with a lower Tg, having polymer chains with a higher freedom degree, will have greater flexibility.

To reduce or avoid use of plasticizers in medical devices such as PVC blood storage bags, it is vital to maintain or increase PVC flexibility.

Flexibility

Stress-strain tests were carried out for studying polymer flexibility. For this it was necessary to use films obtained from a solution containing 1 g of PVC or functionalized PVC in 25 mL of THF. This solution was placed in a petri dish (Ø=10 cm) and the solvent was allowed to evaporate at room temperature.

Test specimen dimensions: 10×70×0.2 mm are obtained from these films.

To perform the Stress-strain test, the test specimen is placed on a dynamometer with a 30 mm gap between jaws, applying a maximum stretching force of 10 kg and a speed of 5 mm/min.

Polymers that showed better surface wettability, lower platelet adhesion on their surface and a molecular weight comparable to the PVC used in the manufacture of commercial blood storage bags were selected to carry out tensile tests. Likewise, tensile tests were carried out on a commercial blood bag (Bag 1: made of PVC having 40% plasticizer DEHP) to compare its properties with some of the studied polymers.

Figure 8:
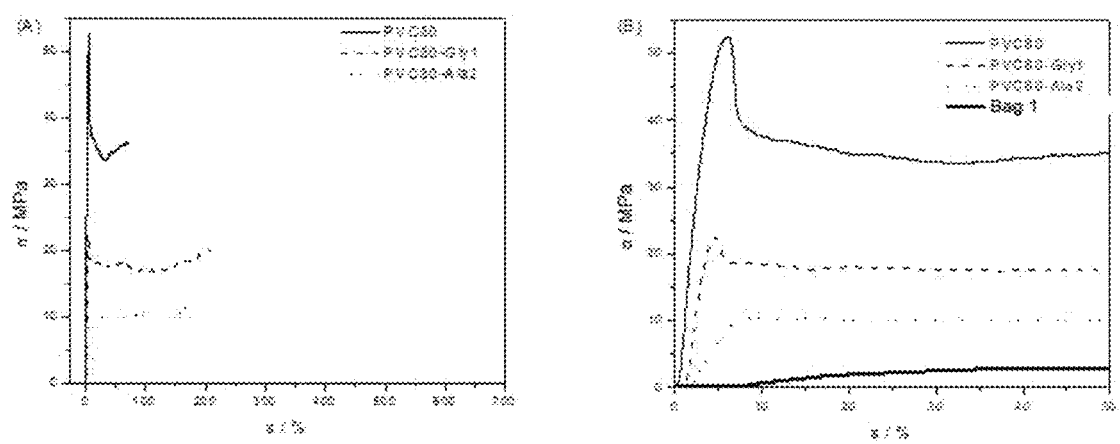
FIG. 8 shows: (A) tensile tests expressed as stress ($\sigma$) as a function of strain ($\varepsilon$) for PVC80, PVC80-Gly1, PVC80-Ala2 and Bag 1 (commercial bag). (B) Elastic deformation region of curves.

FIG. 8 shows tensile tests made for PVC80, PVC80-Gly1, PVC80-Ala2 and Bag 1 (Commercial bag).

FIG. 8 (A) shows that PVC80-Gly1 and PVC80-Ala2 have a plastic behavior, with an elongation at break of 209% and 201%, respectively. PVC80 proved to be very fragile, having an elongation at break of 70.9%. This indicates that PVC80 functionalized with Gly or β-Ala improves the elongation at break of the material.

FIG. 8 (B) shows the extension of the reversible deformation zone. It can be seen that PVC80-Gly1 and PVC80-Ala2 have a lower elasticity module relative to PVC80 (7.2, 2.6 and 12.8 MPa, respectively). This indicates that PVC80-Gly1 and PVC80-Ala2 are more flexible compared to PVC80.

This figure also shows that PVC80-Ala2 does not have a yield point. This indicates that compared to the applied stress, PVC80-Ala2 chains have no major impediment to move one over the other, making deformation close to an elastomeric deformation. This behavior is similar to what occurs with plasticized PVC in the blood bag.

These results indicate that by functionalizing PVC with an amino acid selected from the group of amino acids having hydropathic index between −3.5 and 1.8, such as Gly or β-Ala, PVC80 flexibility is increased and approaches to the flexibility of the commercial blood storage bag.

Blood Compatibility

Blood compatibility of PVC films and PVC functionalized with Gly and β-Ala was studied carrying out platelet adhesion tests on polymer films.

PVC43 was used to perform the tests. However, it is important to note that the platelet adhesion in PVC80 is similar to PVC43, because they have the same hydrophobicity degree. Commercial blood bag, Bag 1, was similarly tested to compare its compatibility with the polymeric films under study.

Figure 9:
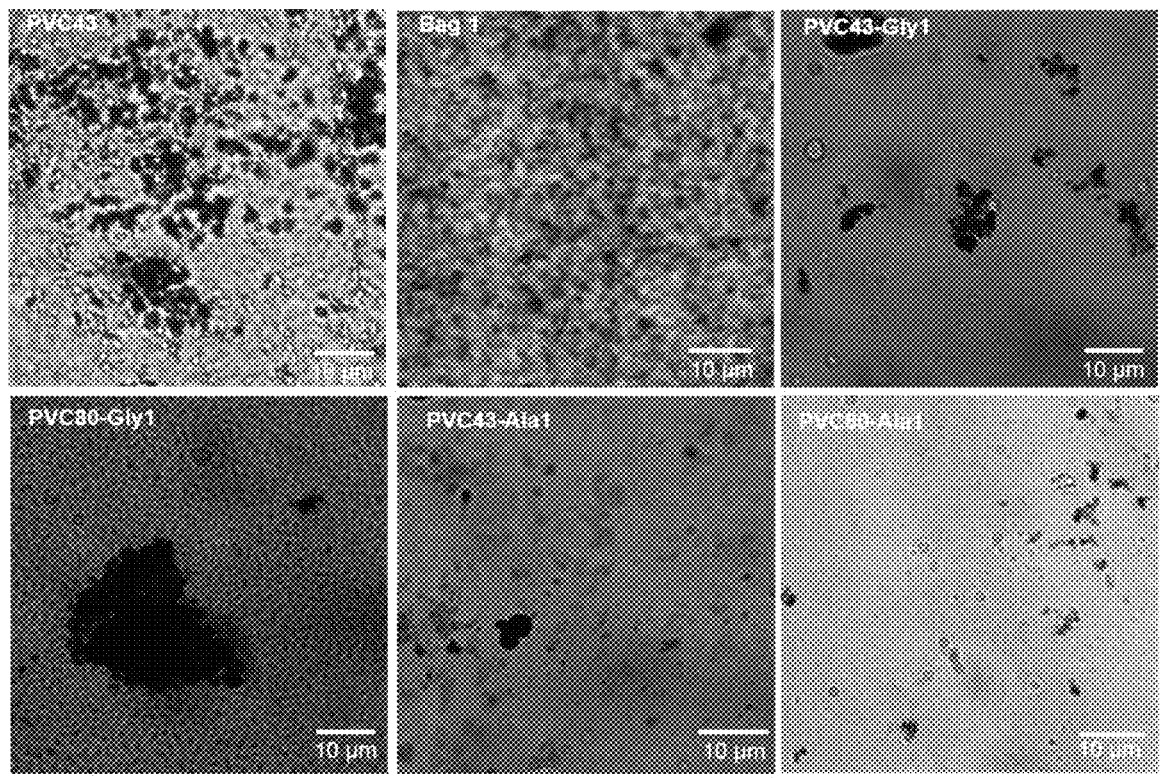
FIG. 9 shows optical photomicrographs of platelets adhered to PVC43 film, Bag 1 and Gly- and β-Ala-functionalized PVC films.

FIG. 9 shows optical images of PVC43, Bag 1 (Commercial bag), PVC43-Gly1, PVC80-Gly1, PVC43-Ala1 and PVC80-Ala1 films obtained after incubation in a platelet solution.

FIG. 9 shows that a large number of platelets adhere to PVC43 film compared to functionalized PVC films. On the other hand, platelet adhesion on Bag 1 (commercial Bag) is almost zero. This could be explained in terms of hydrophobic interactions established between polymer and platelets. Membrane platelets has amino acid residues of hydrophobic nature, which interact with hydrophobic groups present on polymeric film surface. These interactions are greater in PVC, due to the fact that it has a greater number of hydrophobic groups on its surface compared to PVC films functionalized with Gly or β-Ala. On the other hand, the presence of additives in Bag 1 (Commercial Bag) means that there is a low amount of hydrophobic groups on the surface interacting with blood platelets.

Figure 10:
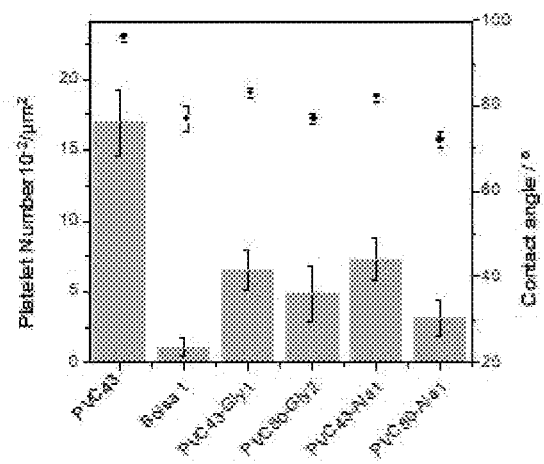
FIG. 10 shows the amount of platelets adhered for each μm$^2$ of surface (bars) and contact angle (circles) for PVC43 film, Bag 1 (commercial bag) and Gly- and β-Ala-functionalized PVC films.

FIG. 10 shows a graph that indicates the amount of platelets adhered for each $\mu m^2$ of surface and contact angle for Bag 1 (Commercial Bag) and for each polymeric film.

FIG. 10 shows values of θav for Bag 1 (commercial Bag) and each polymeric film, which generally are directly proportional to the number of platelets adhered per $\mu m^2$ of surface.

These results confirm that when functionalizing PVC43 or PVC80 with amino acids Gly or β-Ala the obtained polymer minimizes thrombogenic behavior of blood and turns out to be more hemocompatible.

APPLICABILITY EXAMPLES

Example 1

Functionalization of PVC having molecular weight 43,000 g/mol with amino acid Gly was carried out by constant magnetic stirring at 80° C. and under nitrogen atmosphere, using anhydrous DMSO as reaction medium and potassium carbonate as a catalyst. Molar ratio of Gly/$K_2CO_3$/PVC reagents was 1:1:1. Reaction time was 60 min (time 1).

Polymer precipitation was carried out in a MeOH/$H_2O$ mixture at 2:1 (v/v) ratio. Subsequently, the product was obtained by centrifugation at 9,000 rpm for 30 min at 25° C. Finally, the polymer is purified by dissolving in DMSO and precipitation in MeOH/$H_2O$ mixture, and drying to a constant mass in a vacuum oven.

Example 2

Functionalization of PVC of molecular weight 80,000 g/mol with amino acid Gly was carried out by constant magnetic stirring at 80° C. and under a nitrogen atmosphere, using anhydrous DMSO as reaction medium and potassium carbonate as a catalyst. Molar ratio of Gly/$K_2CO_3$/PVC reagents was 2:2:1. Reaction time was 120 min (time 2).

Polymer precipitation was carried out in a MeOH/$H_2O$ mixture at 2:1 (v/v) ratio. Subsequently, the product was obtained by centrifugation at 7,000 rpm for 20 min at 25° C. Finally, the polymer is purified by dissolving in DMSO and precipitation in a MeOH/$H_2O$ mixture, and drying to a constant mass in a vacuum oven.

Example 3

Functionalization of PVC having molecular weight 80,000 g/mol with amino acid β-Ala was carried out by constant magnetic stirring at 80° C. and under nitrogen atmosphere, using anhydrous DMSO as reaction medium and potassium carbonate as a catalyst. Molar ratio of β-Ala/$K_2CO_3$/PVC reagents was 1:1:1. Reaction time was 20 min (time 1).

Polymer precipitation was carried out in an EtOH/$H_2O$ mixture at 2:1 (v/v) ratio. Subsequently, the product was obtained by centrifugation at 10,000 rpm for 25 min at 25° C. Finally, the polymer is purified by dissolving in DMSO and precipitation in a MeOH/$H_2O$ mixture, and drying to a constant mass.

Example 4

Functionalization of PVC having molecular weight 161,000 g/mol with amino acid β-Ala was carried out by constant magnetic stirring at 80° C. and under nitrogen atmosphere, using anhydrous DMSO as reaction medium and potassium carbonate as a catalyst. Molar ratio of β-Ala/$K_2CO_3$/PVC reagents was 3:3:2. In addition, an amount of 12% w/w of DEHP was added. Reaction time was 40 min (time 2).

Polymer precipitation was carried out in a MeOH/$H_2O$ mixture at 2:1 (v/v) ratio. Subsequently, the product was obtained by centrifugation at 8,000 rpm for 20 min at 25° C. Finally, the polymer is purified by dissolving in DMSO and precipitation in MeOH/$H_2O$ mixture, and drying to a constant mass.

Example 5

Functionalized PVCs obtained in the above examples 1 to 4 were used to make blood storage bags, hoses, tubes and intravenous catheters. These medical devices showed an amount of 2 platelets adhered per $\mu m^2$ of surface.

The invention claimed is:
1. A method for producing a functionalized polyvinyl chloride (PVC), CHARACTERIZED in that it comprises the following steps:
    i. mixing a PVC of molecular weight of less than 200,000 g/mol with one or more amino acids (Aa) selected from the group of amino acids having hydropathic index between −3.5 and 1.8 and a catalyst selected from the group of alkaline carbonates having a molar ratio selected from 1:1:1 to 2:2:1 (PVC:amino acid:catalyst), in a dissolution solvent and under inert atmosphere;

ii. stirring the mixture at 1,000 rpm, keeping under a constant temperature between 50° C. and 120° C. for between 20 and 120 minutes;

iii. precipitating the polymer in a precipitation solvent;

iv. centrifuging between 5,000 and 12,000 rpm for 10 to 60 minutes at 25° C. temperature;

v. purifying the functionalized polymer by dissolving in a dissolution solvent and precipitating in a precipitation solvent.

2. The method for producing a functionalized PVC according to claim 1, CHARACTERIZED in that the catalyst used in step (i) is selected from the group of alkaline carbonates such as lithium carbonate ($Li_2CO_3$), sodium carbonate ($Na_2CO_3$) and potassium carbonate ($K_2CO_3$).

3. The method for producing a functionalized PVC according to claim 1, CHARACTERIZED in that the group of amino acids (Aa) with hydropathic index between −3.5 and 1.8 used in step i) are selected from amino acids Gly or β-Ala.

4. The method for producing a functionalized PVC according to claim 1, CHARACTERIZED in that the dissolution solvent used in steps i) and v) is selected from dimethyl sulfoxide (DMSO) anhydrous, cyclohexanone, and dichlorobenzene dimethylformamide.

5. The method for producing a functionalized PVC according to claim 1, CHARACTERIZED in that the precipitation solvent used in steps iii) and v) comprises Methanol/Water ($MeOH/H_2O$) or ethanol/Water ($EtOH/H_2O$) at a 2:1 v/v ratio.

6. The method for producing a functionalized PVC according to claim 1, CHARACTERIZED in that the inert atmosphere uses a gas selected from nitrogen or argon.

7. The method for producing a functionalized PVC according to claim 1, CHARACTERIZED in that to the mixture of step i) is further added a plasticizer, such as di-(2-ethylhexyl)phthalate (DEHP) in an amount of less than 20% w/w, specifically 10% w/w.

8. A functionalized vinyl polyvinyl chloride (PVC) polymer CHARACTERIZED in that it comprises molecular weights of less than 200,000 g/mol; wherein FT-IR spectrum of each functionalized PVC shows the absorption band corresponding to the C=C stretch at 1,630 $cm^{-1}$, the absorption band corresponding to the C=O stretch at 1,734 $cm^{-1}$ and a wide absorption band at 3,340 $cm^{-1}$ corresponding to the O—H stretch vibration; wherein the absorption band corresponding to the N—H stretch is coupled with the band associated with the O—H group and wherein the absorption band corresponding to the C—Cl stretch is observed at 685; wherein its $^1$H NMR spectrum shows an intense signal at 5 ppm, which corresponds to olefin protons (—CH=CH—) present in a large part of the polymer chain, a signal at 2.5 ppm corresponding to the proton of the amino group (—NH—), a signal at 3.3 ppm that corresponds to a coupling of the signals associated with the methine proton linked to the amino acid residue (CH—N) and the methine proton linked to the chlorine atom (CH—Cl), a signal at 4, 2 ppm associated with the methylen proton of the amino acid residue; wherein its $^{13}$C NMR spectrum shows two signals at 40 and 70 ppm corresponding to the presence of methine and methylene carbons, and a signal at 135 ppm corresponding to the olefin carbons (CH=CH) present in the polymer chain.

* * * * *